US011628082B2

(12) United States Patent
Keegan

(10) Patent No.: US 11,628,082 B2
(45) Date of Patent: Apr. 18, 2023

(54) ADJUSTABLE TOE PLATE FOR AN ADJUSTABLE BOOT BRACE

(71) Applicant: William J. Keegan, San Jose, CA (US)

(72) Inventor: William J. Keegan, San Jose, CA (US)

( * ) Notice: Subject to any disclaimer, the term of this patent is extended or adjusted under 35 U.S.C. 154(b) by 304 days.

(21) Appl. No.: 17/178,483

(22) Filed: Feb. 18, 2021

(65) Prior Publication Data
US 2021/0169673 A1 Jun. 10, 2021

Related U.S. Application Data

(63) Continuation-in-part of application No. 16/674,719, filed on Nov. 5, 2019, now abandoned.

(51) Int. Cl.
*A61F 5/00* (2006.01)
*A61F 5/01* (2006.01)

(52) U.S. Cl.
CPC ............ *A61F 5/019* (2013.01); *A61F 5/0127* (2013.01); *A61F 2005/0158* (2013.01); *A61F 2005/0167* (2013.01)

(58) Field of Classification Search
CPC ...... A61F 5/019; A61F 5/0102; A61F 5/0127; A61F 5/013; A61F 5/14; A61F 5/10; A61F 5/37; A61F 5/3715; A61F 5/042; A61F 5/0585; A61F 5/05866; A61F 5/05875; A61H 1/0296; A61H 1/0292; A61H 1/02; A61H 1/0222; A61H 1/0229; A61H 1/0218; A61H 1/0266; A61H 1/0285; A61H 1/0288; A63B 23/085; A63B 23/10; A63B 5/04; A63B 5/0492
USPC ................................................ 602/16, 21, 30
See application file for complete search history.

(56) References Cited

U.S. PATENT DOCUMENTS

| | | | | |
|---|---|---|---|---|
| 2,141,099 A | * | 12/1938 | Walters | A61F 5/0585 602/5 |
| 4,573,457 A | * | 3/1986 | Parks | A43B 13/141 36/31 |
| 4,747,221 A | * | 5/1988 | Hayes | A43B 5/18 36/97 |
| 5,787,611 A | * | 8/1998 | Bonaventure | A43B 5/04 36/119.1 |
| 5,887,591 A | * | 3/1999 | Powell | A61F 5/0127 602/30 |
| 5,897,087 A | * | 4/1999 | Farley | A61B 90/50 248/316.2 |
| 8,979,781 B2 | * | 3/2015 | Cook | A61F 5/05825 602/5 |
| 9,119,437 B2 | * | 9/2015 | Weller | A43B 3/26 |
| 9,370,220 B2 | * | 6/2016 | Slingluff | A43B 13/143 |

* cited by examiner

*Primary Examiner* — Adam Baker
(74) *Attorney, Agent, or Firm* — Bruce A. Lev

(57) ABSTRACT

An adjustable toe plate for an adjustable boot brace adapted to aid in stretching and supporting inflamed tissues and/or an inflamed plantar fascia within a person's foot while healing. The adjustable toe plate includes a toe plate adjustment mechanism to adjust the angle of the toe plate with respect to its foot portion, such that a person can adjust the position and angle of their toes during the healing process.

11 Claims, 9 Drawing Sheets

ADJUSTABLE TOE PLATE FOR AN ADJUSTABLE BOOT BRACE

CROSS-REFERENCE TO RELATED APPLICATION

The present application is related to and claims priority from non-provisional application Ser. No. 16/674,719, filed Nov. 5, 2019 which is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of adjustable boot braces adapted to stretch and support an inflamed tissue and/or inflamed plantar fascia within a person's foot while healing.

2. Description of the Related Art

When a person injures tissues within their foot it may become necessary to stretch and support those tissues during the healing process. The preexisting methods and systems rely on boots that offer means for pulling the person's toes upwardly but does not offer a means for keeping the person's foot stationary while pulling the person's toes upwardly. Therefore, the tissues will not being maximally and/or properly stretched while healing and thereby may not heal properly if at all.

Various attempts have been made to solve the above-mentioned problems such as those found in U.S. Pat. No. 4,577,769 to Ahmad et al; U.S. Pat. No. 6,602,216 to Nordt, III; U.S. Pat. No. 8,226,589 to Darby, II et al; and 2005/0043662 to Price et al. These prior art references are representative of prior adjustable boot devices. None of the above inventions and patents, taken either singly or in combination, is seen to describe the invention as claimed.

BRIEF SUMMARY OF THE INVENTION

In view of the foregoing disadvantages inherent in the known art, the present invention provides an adjustable toe plate for an adjustable boot brace. The general purpose of the present invention, which will be described subsequently in greater detail, is to provide a boot brace adapted to stretch and support an inflamed tissue and/or inflamed plantar fascia within a person's foot while healing.

The instant adjustable boot brace is adapted to help heal inflamed tissues and/or an inflamed plantar fascia within a person's foot. The adjustable boot brace has a plastic outer shell with a soft foam padding inside. There are hook and loop straps that can be adjusted for the most comfortable fit upon a user's leg and foot, and a toe plate adjustment mechanism to adjust the angle of their toes.

The main feature of the instant adjustable boot brace that is an improvement over the prior art boot braces is the way the instant toe plate can isolate the ball of your foot and your toes to be in the exact position that is most comfortable for the person as they work on getting their inflamed tissue and/or inflamed plantar fascia healed, which is done with a toe plate adjustment mechanism to adjust the angle of their toes.

The instant adjustable boot brace incorporates first and second hinge portions respectively attached to its foot portion and the toe plate, a pivot pin, and a tightening mechanism therebetween, such that a user will be able to adjust the angle of the toe plate and give them the most comfort and biggest benefit for stretching an inflamed tissue, and which can increase or decrease the angle of their toes as needed.

The overall structure of the adjustable boot brace is solid with an outer shell being formed from plastic, an inner part formed from a soft foam padding, a toe plate, and a toe plate adjustment mechanism therebetween that keeps the toe plate pivotally attached to the outer shell as the person adjusts the position of their toes. The outer shell is used to hold a person's calf in position and the bottom part of the outer shell is to keep the person's foot held down so only their toes will move in a desired angle that is required. As for comfort and support, five hook and loop straps are incorporated. Two for the calf, two for the foot, and one for the toes.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention constructed and operative according to the teachings of the present invention.

The various embodiments of the present invention will hereinafter be described in conjunction with the appended drawings, wherein like designations denote like elements.

DESCRIPTION OF THE PREFERRED EMBODIMENT

Figure 1:
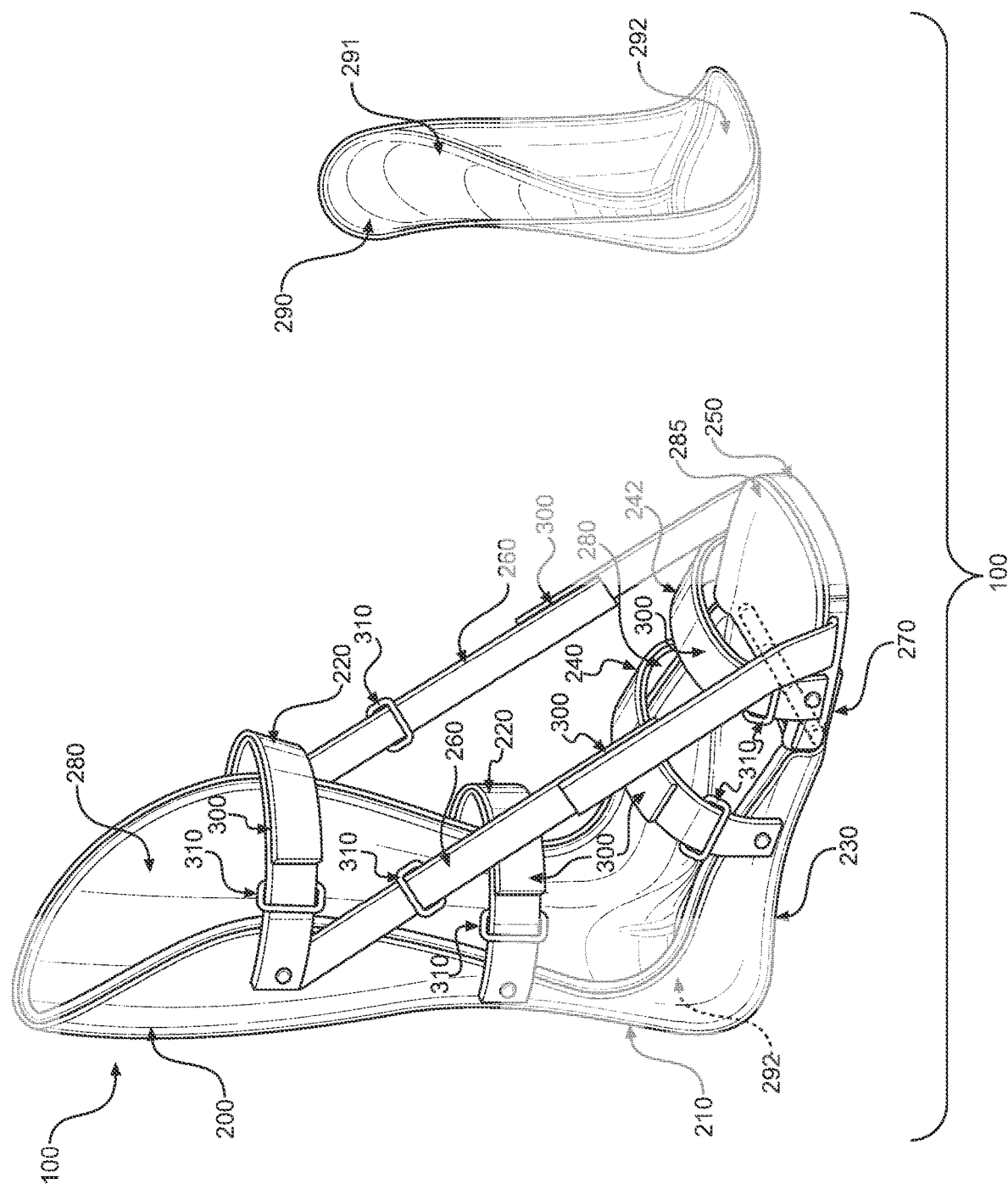
FIG. 1 shows a perspective view illustrating the adjustable boot brace according to an embodiment of the present invention with insert outside of boot shell.
Figure 2:
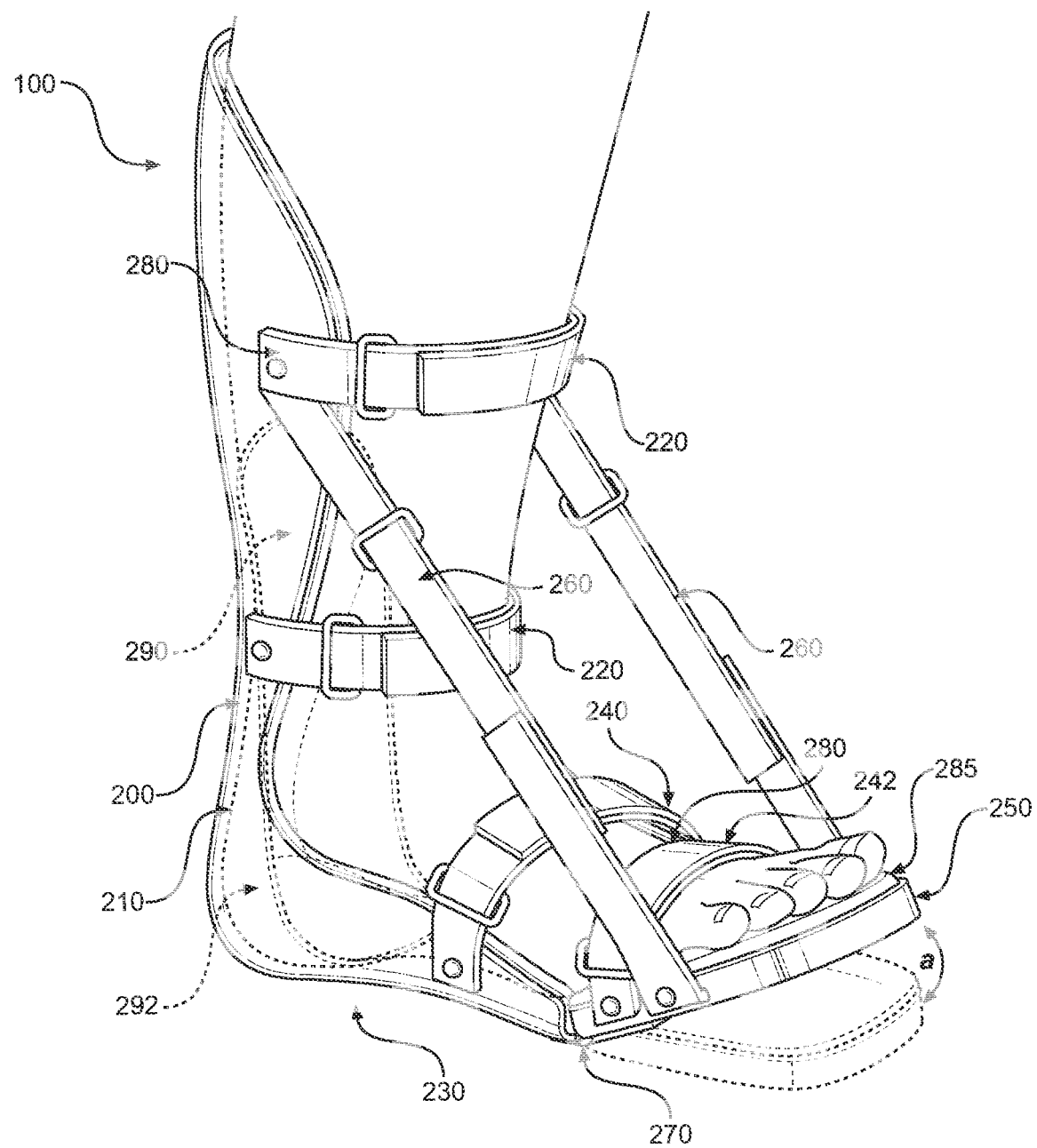
FIG. 2 shows a perspective view the adjustable boot brace in use according to the embodiment of FIG. 1 with insert inside of boot shell.
Figure 3:
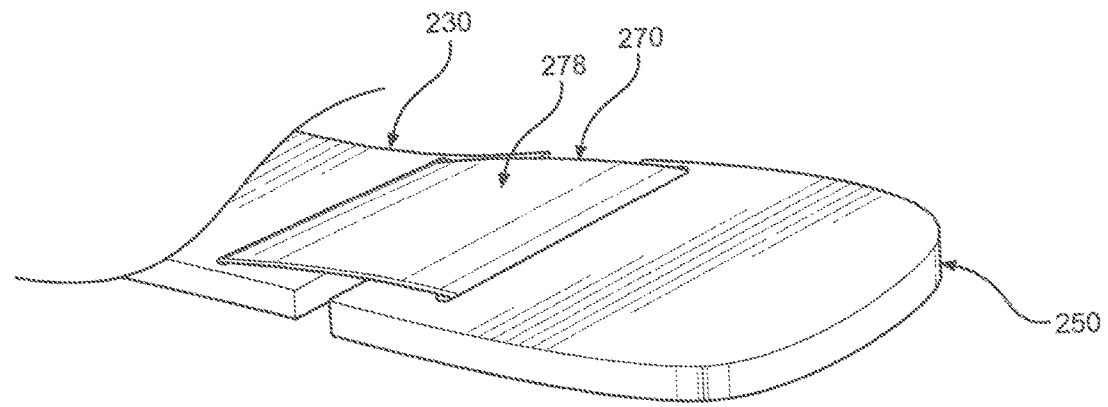
FIG. 3 shows a perspective bottom view illustrating a first embodiment of the hinge of the adjustable boot brace according to the embodiment of FIG. 1.
Figure 4:
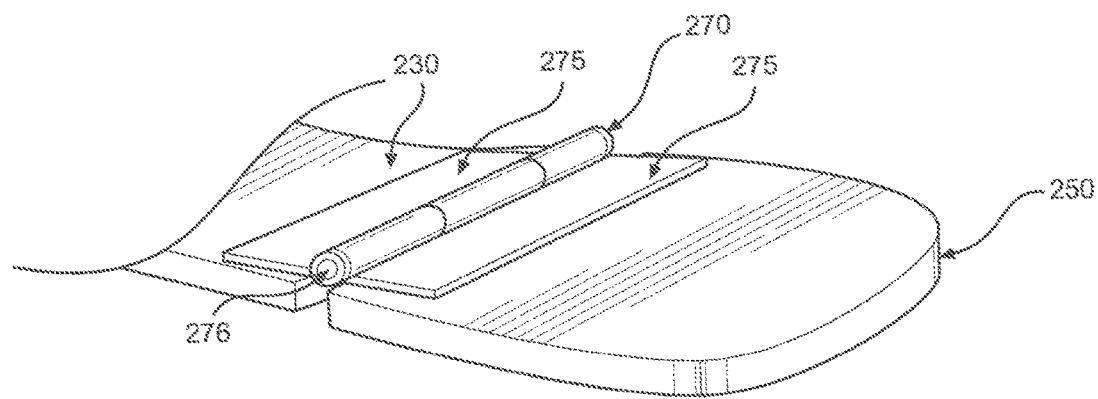
FIG. 4 shows a perspective bottom view illustrating a second embodiment of the hinge of the adjustable boot brace according to the embodiment of FIG. 1.
Figure 5:
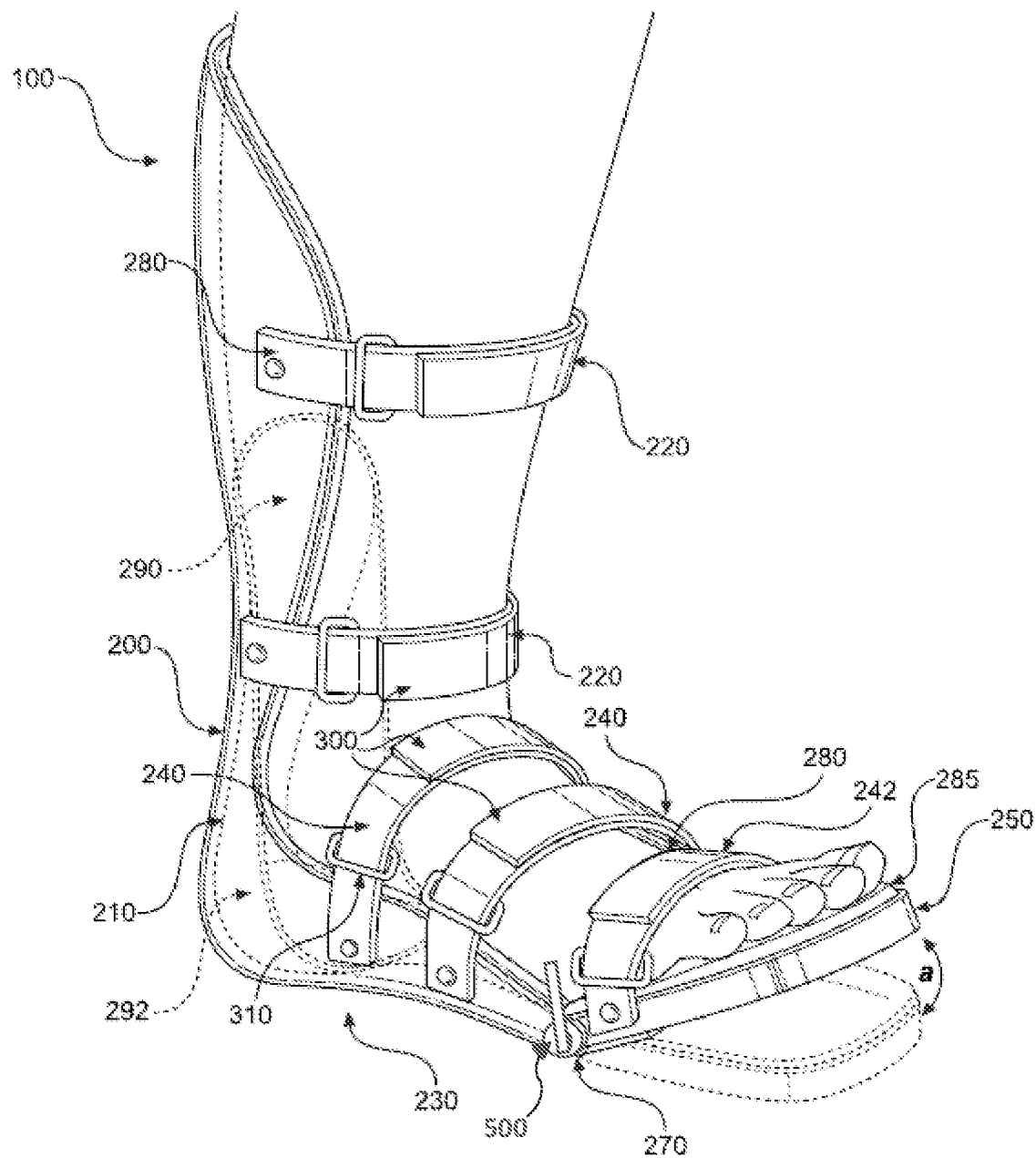
FIG. 5 shows a perspective view illustrating the adjustable boot brace with the toe plate adjustment mechanism attached between the foot portion and the toe plate.
Figure 6:
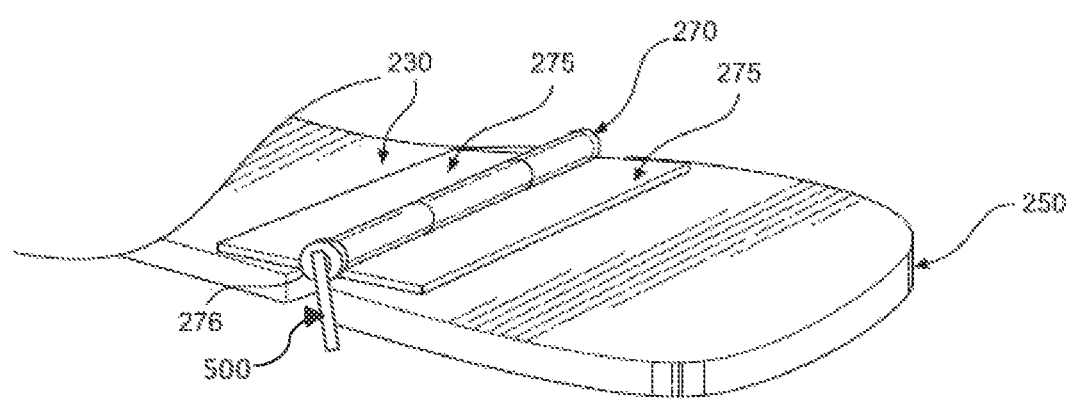
FIG. 6 shows a perspective bottom view illustrating the toe plate adjustment mechanism attached between the foot portion and the toe plate according to the embodiment of FIG. 5.

The adjustable boot brace is adapted to help heal inflamed tissues and/or an inflamed plantar fascia within a person's foot. Referring now to FIGS. 1-4, the original embodiment of the adjustable boot brace 100 is illustrated comprising an outer shell 200 including a rigid calf portion 210 that includes a proximal end, a distal end, a left side, a right side, and at least one adjustable strap 220, wherein the at least one adjustable strap is connected between the left side and the right side thereof, wherein the calf portion is adapted to be placed against and extend along a length of a user's calf, and the at least one adjustable strap is adapted to be placed against a front portion of the user's shin to thereby surround the user's leg and releasably hold the outer shell securely thereto; a rigid foot portion 230 including a proximal end, a distal end, a left side, a right side, and two adjustable straps 240, wherein the two adjustable straps are spaced from one another and connected between the left side and the right side thereof, wherein the foot portion is adapted to be placed against and extend along a length of the bottom of the user's foot, and the two adjustable straps are adapted to be placed against spaced top portions of the user's foot to thereby surround the user's foot and releasably hold the outer shell securely thereto, and wherein the proximal end of the foot portion is rigidly connected to the distal end of the calf portion forming an L-shape; a rigid toe plate 250 including a proximal end, a distal end, a left side, and a right side, wherein the toe plate is adapted to be placed against and extend along a length of the bottom of the toes of the user's foot, and wherein the proximal end of the toe plate is pivotally connected to the distal end of the foot portion 230, and at least one adjustable toe plate strap 260, wherein the at least one adjustable toe plate strap is attached between the rigid toe plate and the proximal end of the rigid calf portion, and is adapted to hold the rigid toe plate at a desired angle, as shown in FIG. 2 as angle "a", with respect to the rigid foot portion. The adjustable boot brace 100 further comprises a hinge 270 connected between the rigid toe plate and the rigid foot portion, which may include two hinge plates 275 and a pivot pin 276 connected therebetween, or as a flexible, stretchable strap 278 connected therebetween, and is adapted to allow the toe plate to pivot with respect to the distal end of the foot portion.

In the original embodiment, there are two spaced adjustable straps 220 connected to the rigid calf portion 210; two adjustable toe plate straps 260, wherein a first adjustable toe plate strap 260 is connected between the left side of the proximal end of the rigid calf portion 210 and the left side of said distal end of said rigid toe plate 250, and wherein a second adjustable toe plate strap 260 is connected between the right side of said proximal end of said rigid calf portion 210 and the right said of said distal end of said rigid toe plate 250. The adjustable straps 220 of the rigid calf portion 210, the adjustable straps 240 of the rigid foot portion 230, and the adjustable straps 260 of the rigid toe plate 250 may be formed from a flexible material and include hook and loop fasteners 300 and length adjusting rings 310 adapted to adjust the lengths thereof respectively. Furthermore, the rigid toe plate 250 further includes an adjustable toe strap 242 connected between said left side and said right side thereof and adapted to hold the user's toes in position upon an upper surface thereof. And, wherein the adjustable toe strap 242 includes hook and loop fasteners 300 and a length adjusting ring 310 adapted to adjust the length thereof. The greatest advantage of the instant configuration over the prior art configurations is that the angle between the rigid toe plate 250 and the rigid foot portion 230, as shown in FIG. 2 as angle "a", is adjustable and can be held in place by the at least one adjustable toe plate strap 260. The closest prior art configurations do not use "rigid" toe plates and simply pull on the tips of a user's toes thereby stretching the muscles, tendons, and ligaments of the toes instead of just the intended area of the plantar fascia area of the user's foot. Therefore, the instant invention is more efficient and will avoid stretching muscles, tendons, and ligaments within a user's toes when in use, especially if/when the user may also have injuries to their toes.

The outer shell and the toe plate may be formed from plastic, fiberglass, aluminum, or copper. The flexible straps may be formed from nylon or polyester. Furthermore, the rigid toe plate may be formed having a substantially rectangular shape.

The adjustable boot brace may further comprise an inner cushioning liner 280 connected to an inner surface of the outer shell and adapted to contact the user's calf and foot when in use, and a toe plate cushioning liner 285 connected to a top surface of said rigid toe plate and adapted to contact the user's toes when in use.

The adjustable boot brace 100 may further comprise at least one adjustment insert 290 adapted to be placed against an inner surface of the rigid calf portion 210 of the outer shell and adapted to adjust the positioning of the user's foot with respect to the rigid calf portion, the rigid foot portion, and the rigid toe plate. The adjustment insert 290 may include at least one curved portion 292 adapted to conform to the shape of the user's heel, and wherein the adjustment insert 290 may be formed from a semi-rigid material and include an outer cushioning layer 291 attached thereto. The at least one adjustment insert 290 may also be formed having other shapes and sizes to thereby adapt to the size and shape of the user's leg and foot. In other situations, a plurality of adjustment insert 290 may be used in conjunction with one another to fit the desired needs of the user.

The improvement to the adjustable boot brace 100 will now be discussed. As shown in FIGS. 5-8, a toe plate adjustment mechanism 400 is disclosed including a first hinge portion 275 attached to the distal end of the foot portion; a second hinge portion 275 attached to the distal end of the proximal end of the toe plate; a pivot pin 270 including a first end portion 271 and a second end portion 272, wherein the pivot pin 270 is adapted to pivotally interconnect the first and second hinge portions 275 and thereby pivotally interconnect the foot portion 230 and the toe plate 250; a first plate 281 movably attached to the first end portion 271 of the pivot pin 270 and is adapted to releasably and frictionally engage one of the first and second hinge portions 275; a second plate 282 attached to the second end portion 272 of the pivot pin 270 and is adapted to frictionally engage one of the first and second hinge portions; and a tightening mechanism 500 attached to the first end portion of the pivot pin and adjacent the first plate. The tightening mechanism 500 is adapted to releasably press against the first plate 281, move the first plate 281 to be in contact with the one of the first and second hinge portions 275, move the second plate 282 to be in contact with the one of the first and second hinge portions 275, thereby creating sufficient friction between the first and second plates and the first and second hinge portions to releasably hold the first and second hinge portions in position at a desired angle (a) with respect to one another, and thereby releasably hold the toe plate 250 at a desired angle with respect to the rigid foot portion 230.

The toe plate adjustment mechanism 500 may further comprise a third plate 283 including a series of spaced teeth 286 located on an outer surface thereof, wherein the third plate 283 is attached to an outer portion of one of the first and second hinge portions 275 adjacent the second plate 282; and wherein the second plate 282 further includes a series of spaced teeth 287 located on an inner surface thereof.

Figure 7:
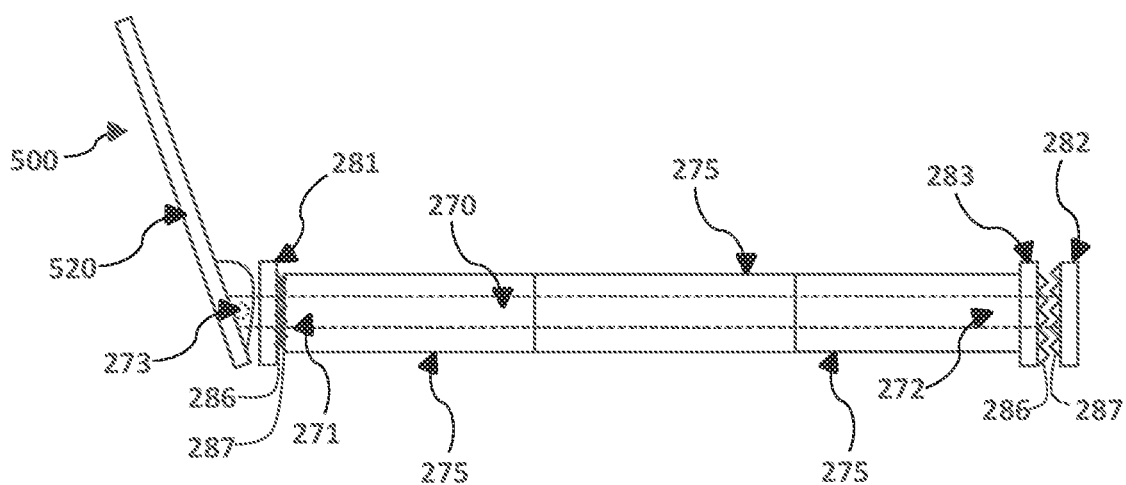
FIG. 7 shows a front view illustrating the toe plate adjustment mechanism according to the embodiment of FIG. 5 incorporating a cam lever.
Figure 8:
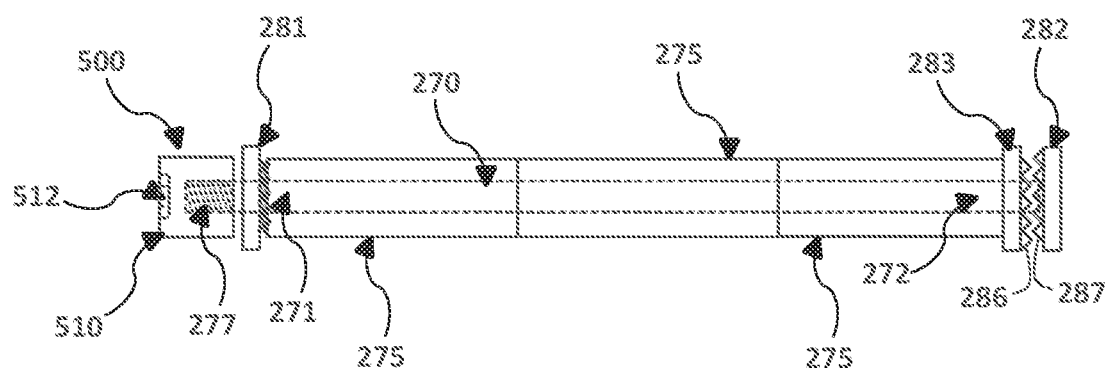
FIG. 8 shows a side view illustrating the toe plate adjustment mechanism incorporating a tightening bolt.
Figure 9A:
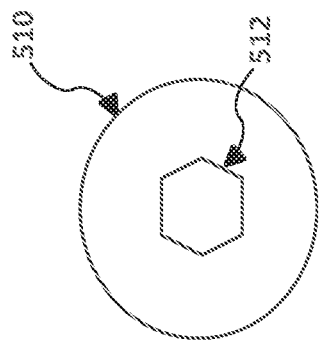
FIGS. 9a-9d shows side views illustrating the different shapes of the driver indentation within the head of the tightening bolt.
Figure 9B:
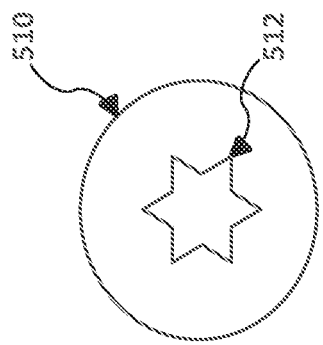
Figure 9C:
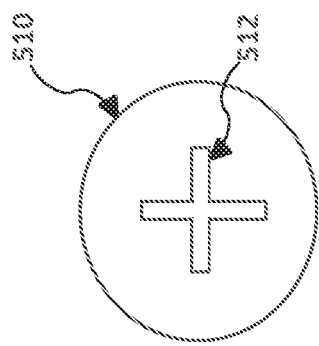
Figure 9D:
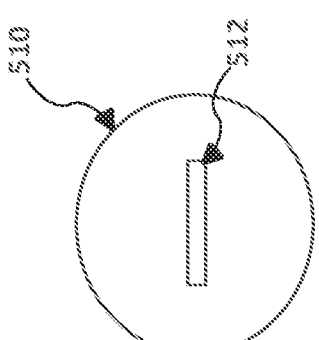

As shown in FIGS. 7 and 8, the series of spaced teeth 287 of the second plate 282 are adapted to releasably engage the series of spaced teeth 286 of the third plate 283 when the tightening mechanism 500 is tightened, and are adapted to disengage with the series of spaced teeth 286 of the third plate 283 when the tightening mechanism 500 is loosened, to thereby more securely releasably hold the first and second hinge portions 275 in position at a desired angle (a) with respect to one another, and thereby releasably hold the toe plate 250 at a desired angle (a) with respect to the rigid foot portion 230.

As also shown in FIGS. 7 and 8, the first plate 281 may also have a series of spaced teeth 286 thereon, and said one of the first and second hinge portions 275 adjacent said first plate 281 may also have a series of spaced teeth 287 thereon, to thereby further releasably hold the toe plate 250 at a desired angle (a) with respect to the rigid foot portion 230.

As shown in FIG. 8, the first end portion 271 of the pivot pin 270 may further include threads 277 thereon, and the tightening mechanism 500 include a tightening bolt 510 including an interior cylindrical wall forming a hollow cylindrical interior volume adapted to receive the first end portion 271 of the pivot pin 270, and including threads 277 thereon, wherein the threads 277 of the tightening bolt 510 are adapted to engage the threads 277 of the first end portion 271 of the pivot pin 270, such that the tightening bolt 510 can be turned to tighten or loosen the toe plate adjustment mechanism 500 to releasably hold the first and second hinge portions 275 in position at a desired angle (a) with respect to one another, and thereby releasably hold the toe plate 250 at a desired angle (a) with respect to the rigid foot portion 230. As shown in FIGS. 9a-9d, the tightening bolt 510 may include a head having a driver indentation 512 in the shape of a flathead, crosshead, 6-point star, or polygon.

As shown in FIG. 7, the tightening mechanism 500 may include a cam lever 520 pivotally connected to the first end portion 271 of the pivot pin 270 via a lever pin 273 of the first end portion 271, and is shaped and adapted to releasably press against and move the first plate 281 into contact with the one of said first and second hinge portions 275 when the cam lever 520 is pivoted in one direction, and released from pressing against the first plate 281 when the cam lever 520 is pivoted in the opposite direction.

The cam lever 520 also includes an aperture therethrough, wherein the aperture of the cam lever 520 pivotally engages with the lever pin 273 of the first end portion of the pivot pin to thereby pivotally engage with the pivot pin 270.

The pivot pin 270 can also be securely attached to the second hinge portion 275 of the toe plate 250, such that the cam lever 520 can pivot the toe plate 250 to a desired angle (a) with respect to the foot portion 230 before locking it in position.

Figure 10:
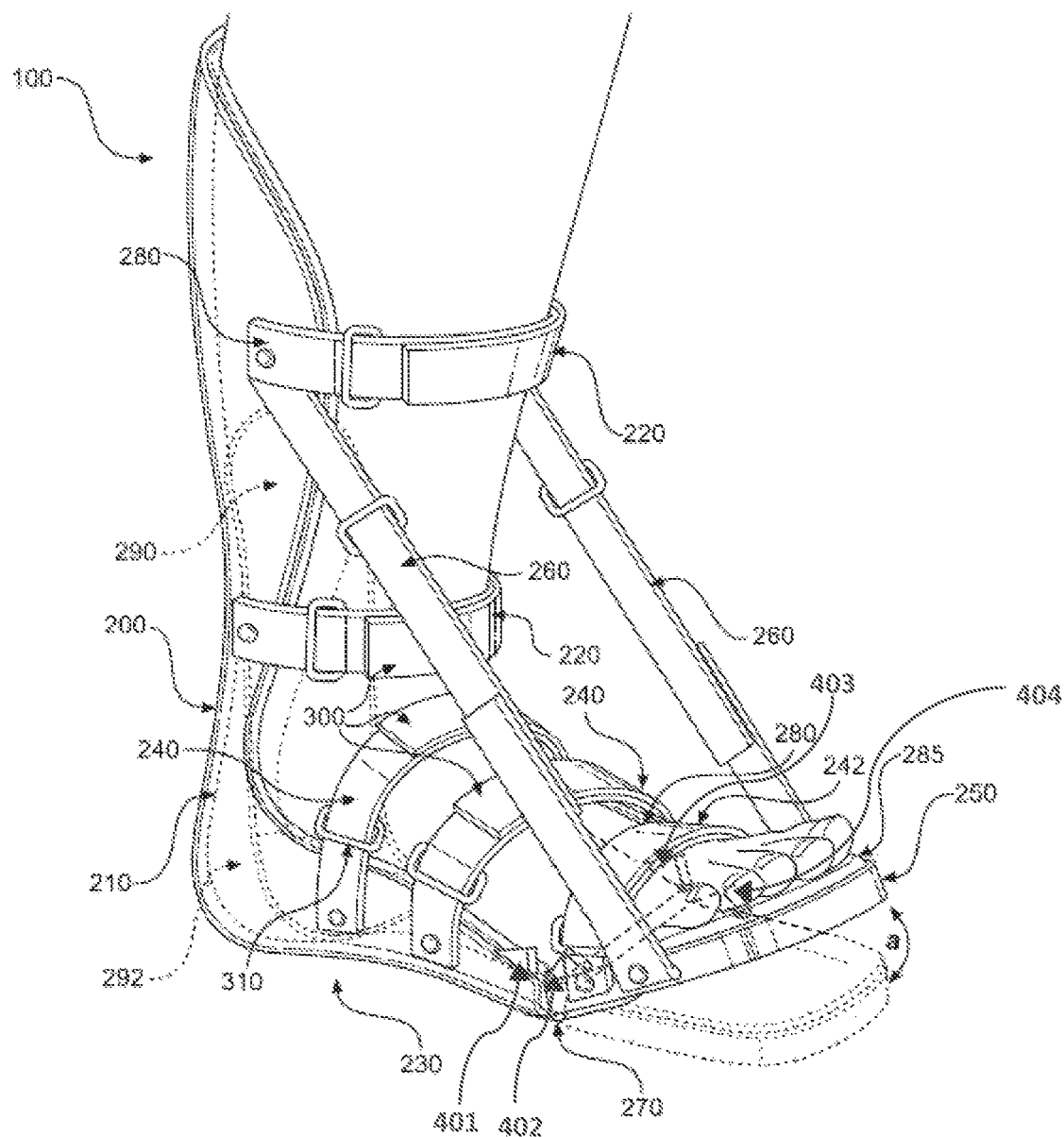
FIG. 10 shows a perspective view illustrating the adjustable boot brace incorporating stop members limiting the angle to which toe plate can pivot with respect to said foot portion.

As shown in FIG. 10, the toe plate adjustment mechanism 400 may further comprise a first stop member 401 attached to a first side edge of the distal end of the foot portion, and a second stop member 402 attached to a first side edge of the proximal end of the toe plate, wherein the second stop member is adapted to contact the first stop member to thereby limit the angle to which the toe plate can pivot with respect to the foot portion. Furthermore, the toe plate adjustment mechanism 400 may further comprise a third stop member 403 attached to a second side edge of the distal end of the foot portion, and a fourth stop member 404 attached to a second side edge of the proximal end of the toe plate, wherein the third stop member is adapted to contact the fourth stop member when the first stop member contacts the second stop member to thereby limit the angle to which said toe plate can pivot with respect to said foot portion. As such, the toe plate 250 defines a flat plane and the foot portion 230 defines a flat plane, wherein the first and second and third and fourth stop members prevent the toe plate flat plane from pivoting more than 90 degrees with respect to the foot portion flat plane.

It should be noted that the steps described in the method of use can be carried out in many different orders according to user preference. The use of "step of" should not be interpreted as "step for", in the claims herein and is not intended to invoke the provisions of 35 U.S.C. § 112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. In an adjustable boot brace including:
an outer shell including:
a rigid calf portion including:
a proximal end;
a distal end:
a left side;
a right side; and
at least one adjustable strap;
wherein said at least one adjustable strap is connected between said left side and said right side thereof;
wherein said calf portion is adapted to be placed against and extend along a length of a user's calf, and said at least one adjustable strap is adapted to be placed against a front portion of the user's shin to thereby surround the user's leg and releasably hold said outer shell securely thereto;
a rigid foot portion including:
a proximal end;
a distal end:
a left side;
a right side; and
at least one adjustable strap;
wherein said at least one adjustable strap is connected between said left side and said right side thereof;
wherein said foot portion is adapted to be placed against and extend along a length of the bottom of the user's foot, and said at least one adjustable strap is adapted to be placed against a top portion of the user's foot to thereby surround the user's foot and releasably hold said outer shell securely thereto; and
wherein said proximal end of said foot portion is rigidly connected to said distal end of said calf portion forming an L-shape; and
a rigid toe plate including:
a proximal end;
a distal end:
a left side; and
a right side;
wherein said toe plate is adapted to be placed against and extend along a length of the bottom of the toes of the user's foot; and
wherein said proximal end of said toe plate is pivotally connected to said distal end of said foot portion;
the improvement comprising:
a toe plate adjustment mechanism including:
a first hinge portion:
wherein said first hinge portion is attached to said distal end of said foot portion;
a second hinge portion:
wherein said second hinge portion is attached to said distal end of said proximal end of said toe plate;
a pivot pin including:
a first end portion;
a second end portion;
wherein said pivot pin is adapted to pivotally interconnect said first and second hinge portions, and thereby pivotally interconnect said foot portion and said toe plate;
a first plate;
wherein said first plate is movably attached to said first end portion of said pivot pin and is adapted to releasably and frictionally engage one of said first and second hinge portions;
a second plate;
wherein said second plate is attached to said second end portion of said pivot pin and is adapted to frictionally engage one of said first and second hinge portions; and
a tightening mechanism;
wherein said tightening mechanism is attached to said first end portion of said pivot pin and adjacent said first plate;
wherein said tightening mechanism is adapted to releasably press against said first plate, move said first plate to be in contact with said one of said first and second hinge portions, move said second plate to be in contact with said one of said first and second hinge portions, thereby creating sufficient friction between said first and second plates and said first and second hinge portions to thereby releasably hold said first and second hinge portions in position at a desired angle with respect to one another, and thereby releasably hold said toe plate at a desired angle with respect to said rigid foot portion.

2. The adjustable boot brace of claim 1, wherein said toe plate adjustment mechanism further comprises:
a third plate including:
a series of spaced teeth;
wherein said series of spaced teeth are located on an outer surface thereof;
wherein said third plate is attached to an outer portion of one of said first and second hinge portions adjacent said second plate; and
wherein said second plate further includes:
a series of spaced teeth;
wherein said series of spaced teeth are located on an inner surface thereof;
wherein said series of spaced teeth of said second plate are adapted to releasably engage said series of spaced teeth of said third plate when said tightening mechanism is tightened, and are adapted to disengage with said series of spaced teeth of said third plate when said tightening mechanism is loosened, to thereby securely releasably hold said first and second hinge portions in position at a desired angle with respect to one another, and thereby releasably hold said toe plate at a desired angle with respect to said rigid foot portion.

3. The adjustable boot brace of claim 2, wherein said toe plate adjustment mechanism wherein:
said one of said first and second hinge portions further includes:
a series of spaced teeth;
wherein said series of spaced teeth are located on an outer surface thereof adjacent said first plate; and
wherein said first plate further includes:
a series of spaced teeth;
wherein said series of spaced teeth are located on an inner surface thereof;
wherein said series of spaced teeth of said first plate are adapted to releasably engage said series of spaced teeth of said one of said first and second hinge portions when said tightening mechanism is tightened, and are adapted to disengage with said series of spaced teeth of said one of said first and second hinge portions when said tightening mechanism is loosened, to thereby more securely releasably hold said first and second hinge portions in position at a desired angle with respect to one another, and thereby further releasably hold said toe plate at a desired angle with respect to said rigid foot portion.

4. The adjustable boot brace of claim 1, wherein said first end portion of said pivot pin further includes threads thereon; and wherein said tightening mechanism further includes:
a tightening bolt including:
an interior cylindrical wall;
wherein said interior cylindrical wall forms a hollow cylindrical interior volume adapted to receive said first end portion of said pivot pin; and
wherein said interior cylindrical wall includes threads thereon;
wherein said threads of said tightening bolt are adapted to engage said threads of said first end portion of said pivot pin, such that said threaded bolt can be turned to tighten or loosen said toe plate adjustment mechanism to releasably hold said first and second hinge portions in position at a desired angle with respect to one another, and thereby releasably hold said toe plate at a desired angle with respect to said rigid foot portion.

5. The adjustable boot brace of claim 4, wherein said tightening bolt includes a head having a driver indentation chosen from a group of driver indentations consisting of flathead, crosshead, 6-point star, and polygonal.

6. The adjustable boot brace of claim 1, wherein said tightening mechanism further includes:
a cam lever;
wherein said cam lever is pivotally connected to said first end portion of said pivot pin, and is shaped and adapted to releasably press against and move said first plate into contact with said one of said first and second hinge portions when said cam lever is pivoted in one direction, and released from pressing against said first plate when said cam lever is pivoted in the opposite direction.

7. The adjustable boot brace of claim 6, wherein said first end portion of said pivot pin further includes a lever pin thereon; and wherein said cam lever includes:
an aperture therethrough;
wherein said aperture of said cam lever is adapted to pivotally engage with said lever pin of said first end portion of said pivot pin to thereby pivotally hold said cam lever upon said pivot pin.

8. The adjustable boot brace of claim 6, wherein said pivot pin is securely attached to said second hinge portion of said toe plate, such that said cam lever can pivot said toe plate to a desired angle with respect to said foot portion before locking it in position.

9. The adjustable boot brace of claim 1, wherein the improvement further comprises:
a first stop member;
wherein said first stop member is attached to a first side edge of said distal end of said foot portion; and
a second stop member;
wherein said second stop member is attached to a first side edge of said proximal end of said toe plate;
wherein said second stop member is adapted to contact said first stop member to thereby limit the angle to which said toe plate can pivot with respect to said foot portion.

10. The adjustable boot brace of claim 9, wherein the improvement further comprises:
a third stop member;
wherein said third stop member is attached to a second side edge of said distal end of said foot portion; and
a fourth stop member;
wherein said fourth stop member is attached to a second side edge of said proximal end of said toe plate;
wherein said third stop member is adapted to contact said fourth stop member when said first stop member contacts said second stop member to thereby limit the angle to which said toe plate can pivot with respect to said foot portion.

11. The adjustable boot brace of claim 9, wherein said toe plate defines a flat plane; wherein said foot portion defines a flat plane; and wherein said first and second stop members prevent said toe plate flat plane from pivoting more than 90 degrees with respect to said foot portion flat plane.

* * * * *